(12) United States Patent
Suzuki

(10) Patent No.: US 10,180,404 B2
(45) Date of Patent: Jan. 15, 2019

(54) X-RAY ANALYSIS DEVICE

(71) Applicant: SHIMADZU CORPORATION, Kyoto-shi, Kyoto (JP)

(72) Inventor: Keijiro Suzuki, Kyoto (JP)

(73) Assignee: SHIMADZU CORPORATION, Kyoto-shi, Kyoto (JP)

(*) Notice: Subject to any disclaimer, the term of this patent is extended or adjusted under 35 U.S.C. 154(b) by 0 days.

(21) Appl. No.: 14/700,838

(22) Filed: Apr. 30, 2015

(65) Prior Publication Data
US 2016/0320322 A1    Nov. 3, 2016

(51) Int. Cl.
| | |
|---|---|
| *G01N 23/22* | (2018.01) |
| *H05G 1/02* | (2006.01) |
| *G01N 23/223* | (2006.01) |
| *G21K 1/04* | (2006.01) |

(52) U.S. Cl.
CPC ............ *G01N 23/223* (2013.01); *G21K 1/04* (2013.01)

(58) Field of Classification Search
CPC ................................ G01N 23/223; G21K 1/04
See application file for complete search history.

(56) References Cited

U.S. PATENT DOCUMENTS

| | | | | |
|---|---|---|---|---|
| 4,203,037 A | * | 5/1980 | Gur ....................... | A61B 6/0414 378/146 |
| 2013/0251100 A1 | * | 9/2013 | Sasaki .................. | G01N 23/046 378/20 |

FOREIGN PATENT DOCUMENTS

| | | |
|---|---|---|
| JP | 11-264806 A | 9/1999 |
| JP | 2003-207467 A | 7/2003 |

* cited by examiner

*Primary Examiner* — Eliza Osenbaugh-Stewart
(74) *Attorney, Agent, or Firm* — Sughrue Mion, PLLC

(57) ABSTRACT

Collimator unit between X-ray tube and sample includes a plurality of collimator plates and displacement mechanisms, which move the collimator plates in interlocked fashion so as to locate the centers of through-holes on a line connecting X-ray focal point to an arbitrary point on the sample W, thereby suppressing the shading of X-rays due to the axis of the through-holes of the collimator unit becoming diagonal to the line connecting the X-ray focal point and the point on the sample.

6 Claims, 2 Drawing Sheets

X-RAY ANALYSIS DEVICE

TECHNICAL FIELD

The present invention relates to an X-ray analysis device, more specifically, to an X-ray analysis device having a simple mapping function.

BACKGROUND ART

In an X-ray analysis device, generally, fluorescent X-rays (characteristic X-rays) generated by irradiating a sample with excitation X-rays are detected and the energy (wavelength) and intensity (dose) of the fluorescent X-rays are determined. Since the fluorescent X-rays (characteristic X-rays) emitted from a sample have element-specific energy (wavelength), by determining the energy (wavelength) of the fluorescent X-rays, it is possible to identify the elements contained in the sample, and based on the intensity (dose) thereof, it is possible to find out the concentration of the elements.

X-ray analysis devices are classified according to the manner of analysis of the energy (wavelength) of fluorescent X-rays as energy dispersive or wavelength dispersive. In an energy dispersive X-ray analysis device, fluorescent X-rays emitted from a sample are directly detected by an X-ray detector comprising a semiconductor detector or the like, and using the fact that the wave height of the detection output is correlated with the energy of the X-rays, the output signal of the X-ray detector is sorted according to wave height, and the dose for each wave height, and thus for each energy, is determined. On the other hand, in a wavelength dispersive X-ray analysis device, fluorescent X-rays emitted from the sample are separated by wavelength using an analyzing crystal or the like, and the X-ray dose at each wavelength is detected.

In X-ray analysis devices as described above, a technique called mapping analysis is known. Mapping analysis is an analytical method in which the irradiation location of X-rays on a sample is successively changed, fluorescent X-rays are detected at each X-ray irradiation location, and analysis is performed as described above to determine the concentration distribution of elements at each location of the sample.

In order to perform this sort of mapping analysis, usually, a configuration is employed whereby the sample is secured to a displacement mechanism such as an XY stage, and that displacement mechanism is driven to move the sample in relation to a fixed X-ray irradiation location of excitation X-rays from the X-ray tube.

Figure 4:
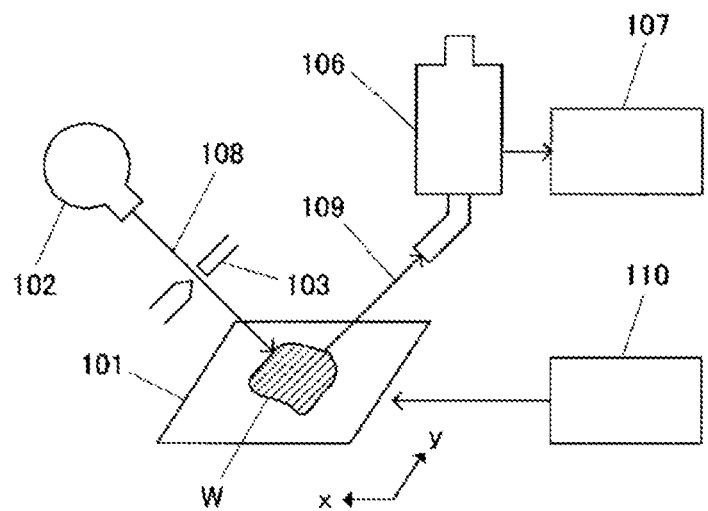

Taking an energy dispersive X-ray analysis device as an example, the essential parts of the configuration of a conventional device capable of mapping analysis are shown in FIG. 4. A sample W is positioned and secured on an XY stage 101, and X-rays from an X-ray tube 102 are irradiated via a collimator 103 as excitation X-rays 108 onto that sample W. Fluorescent X-rays 109 emitted from the sample W as a result of this irradiation are inputted into an X-ray detector 106 and are detected. The output of the X-ray detector 106 is acquired by a measurement circuit 107 such as a multichannel analyzer and is amplified, after which wave height analysis and counting of signals at each wave height are performed.

The XY stage 101 is driven under the control of a stage controller 110, and moves and positions the sample W so that the irradiation location of excitation X-rays 108 on the sample W successively changes within a preset range (for example, see Patent Literature 1).

In this way, since the excitation X-ray irradiation location is fixed and the sample W is moved, an XY stage is necessary, and in the case of a configuration capable of handling relatively large samples, the device becomes bulky, and to resolve this problem, the technique of moving the collimator so as to change the irradiation location of excitation X-rays on the sample has been proposed (for example, see Patent Literature 2).

Namely, according to the technique disclosed in Patent Literature 2, the X-ray tube and sample are fixed and a collimator having a through-hole, disposed between them, is moved, thereby changing the X-ray irradiation location on the sample.

PRIOR ART LITERATURES

Patent Literatures (Patent Literature 1) Japanese Unexamined Patent Application Publication H11-264806
(Patent Literature 2) Japanese Unexamined Patent Application Publication 2003-207467

SUMMARY OF THE INVENTION

Problem to be Solved by the Invention

However, a configuration in which mapping is carried out by providing an XY stage for moving the sample becomes bulky as described above, and at the same time, when one wishes to simply carry out mapping, it is still necessary to secure the sample to the XY stage, so there is also the problem that rapid simple mapping cannot be carried out.

Furthermore, with the technique described in Patent Literature 2, in which the excitation X-ray irradiation location is changed by moving the collimator, there is the problem that an X-ray shadow will occur due to the collimator depending on the excitation X-ray irradiation location, thus narrowing the X-ray irradiation region on the sample.

Namely, the collimator used in analysis devices of this type has a through-hole formed in a collimator main body which has a predetermined thickness, but a collimator is a part fundamentally intended for forming parallel light rays, so if the collimator main body is thin, it will not be possible to prevent the spread of X-rays emitted from the focal point of the X-ray tube, making it impossible for the collimator to play the role of a collimator, and the function of blocking X-rays will also decline.

Due to these facts, the collimator main body needs to have a certain minimal thickness, but if the collimator is moved in parallel in order to change the irradiation location of excitation X-rays, there is the problem that, depending on the irradiation location, the axis of the through-hole in the collimator will no longer be parallel to the line connecting the focal point of the X-ray tube and the X-ray irradiation location on the sample, so X-rays from the X-ray focal point will enter diagonally into the through-hole which has a length equivalent to the thickness of the collimator, and X-rays will be blocked by the inner wall of the through-hole, as a result of which the X-ray irradiation region on the sample will become narrower.

Patent Literature 2 points out the existence of this problem, and as a countermeasure thereto, describes a method of moving the collimator in a circular arc centered on the X-ray focal point.

However, in order to move the collimator in a circular arc centered on the X-ray focal point, a mechanism moving the collimator in a circular arc virtually centered on the X-ray focal point becomes necessary, leading to a very complex and bulky device configuration, so rather than using this sort of mechanism, using a conventional mechanism which moves the sample with an XY stage would provide for a simpler device configuration.

The present invention was made in view of these circumstances, its purpose being to provide an X-ray analysis device which is capable of performing simple mapping analysis by changing the irradiation location of excitation X-rays on a sample by means of a simple configuration without moving the sample, and is also capable of suppressing the shading of excitation X-rays.

Means for Solving the Problem

The X-ray analysis device of the present invention, intended to solve the aforementioned problem, is an X-ray analysis device wherein X-rays from an X-ray tube are irradiated via a collimator unit onto a sample, fluorescent X-rays generated due to such irradiation are detected by an X-ray detector, and information concerning elements contained in the sample is obtained from the detection results, characterized in that: said collimator unit comprises a plurality of flat collimator plates with a through-hole formed in their thickness direction; these collimator plates are arranged parallel to each other and are configured such that each collimator plate is movable in the direction of spread of the plates by driving of an individual displacement mechanism; and said displacement mechanisms are driven in interlocked fashion under the control of a controller so as to locate the centers of the through-holes of said collimator plates on a line connecting the focal point of said X-ray tube and an arbitrary point on the sample, and are configured so as to move the irradiation location of X-rays from said X-ray tube on the sample by moving said collimator plates.

In the present invention, to solve the problem, the collimator, which is provided between the X-ray tube and the sample and serves to make the excitation X-rays substantially parallel while at the same time narrowing the X-rays to the required irradiation area on the sample, is not made into a form wherein a through-hole is created in a single collimator main body as in the prior art, but is rather made up of multiple collimator plates with through-holes formed in their thickness direction, and these collimator plates are separately moved in interlocked fashion so as to align the through-holes of each collimator plate in a line connecting the focal point of the X-ray tube to a point on the sample.

Namely, if the collimator plates, each with a through-hole formed therein, are moved in interlocked fashion so that the center of each through-hole is positioned on a line liking the X-ray focal point to an arbitrary point on the sample, the set of through-holes of the collimator plates take on a state very close to that of a single through-hole oriented diagonally to the X-ray focal point. In this way, it is possible to suppress the occurrence of X-ray shadow as occurs in the prior art, where the irradiation location of excitation X-rays on the sample is changed by moving a single through-hole in parallel.

Therefore, with the configuration of the present invention, it is possible to suppress the generation of X-ray shadow due to the inner wall of the through-hole of the collimator while changing the irradiation location of excitation X-rays on the sample through movement of the collimator, allowing simple mapping analysis on the basis of a simple configuration.

Effect of the Invention

According to the present invention, the irradiation location of excitation X-rays on the sample is changed by moving multiple collimator plates in interlocked fashion so as to arrange the centers of the through-holes of the collimator plates on a line connecting the X-ray irradiation location on the sample and the X-ray focal point, thus allowing simple mapping analysis without providing an XY stage for moving the sample, allowing the device configuration to be made more compact and at the same time allowing mapping analysis simply by placing the sample, for example, onto a sample tray, without specially securing it, thus allowing mapping analysis to be carried out rapidly.

Moreover, it becomes possible to suppress X-ray shadow, which occurs when a single collimator having the required thickness is moved in a plane as in the prior art, whereupon the line connecting the X-ray focal point and the X-ray irradiation location on the sample ceases to be parallel to the axis of the through-hole in the collimator. Compared to the countermeasure technique of displacing a single collimator in a circular arc about the X-ray focal point in order to prevent such X-ray shadow, the shadow suppressing effect here is not complete, but the device configuration can be greatly simplified.

BRIEF DESCRIPTION OF THE DRAWINGS (FIG. 1) A diagram of the main parts of an embodiment of the present invention.

(FIG. 2) An illustration of the operation of an embodiment of the present invention.

Figure 2:
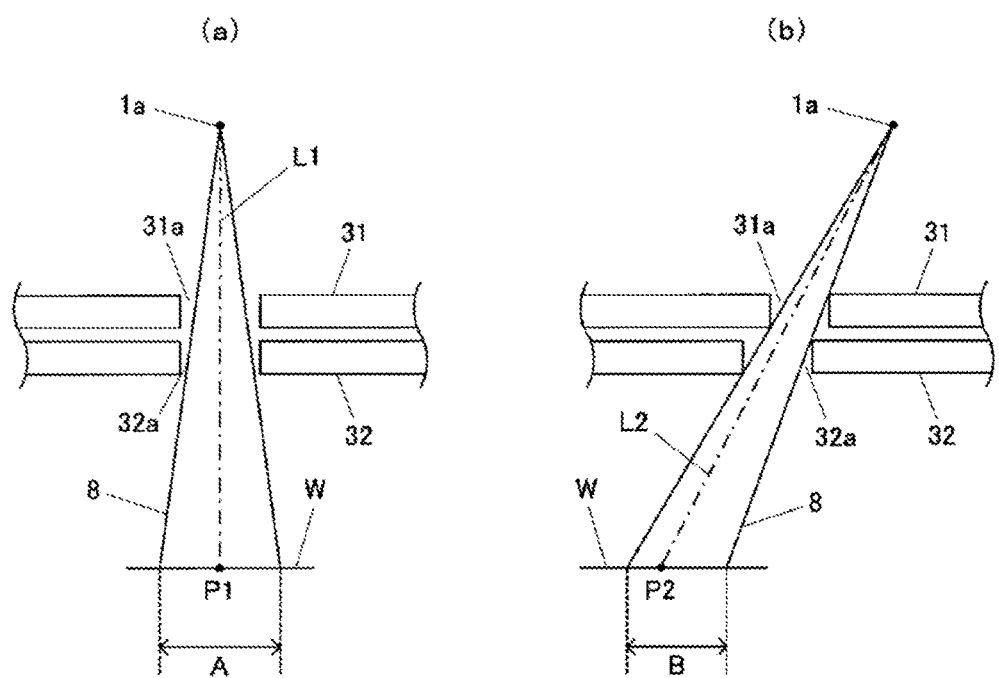

(FIG. 3) An illustration of the operation of a comparison example to FIG. 2, being a drawing intended to explain the occurrence of X-ray shadow when a single collimator having the required thickness is moved in a plane.

(FIG. 4) A diagram of the main parts of an X-ray analysis device having a conventional mapping analysis function in which the sample is moved by means of an XY stage.

DETAILED DESCRIPTION OF THE EXEMPLARY EMBODIMENTS

An embodiment of the present invention will be described below with reference to the drawings.

Figure 1:
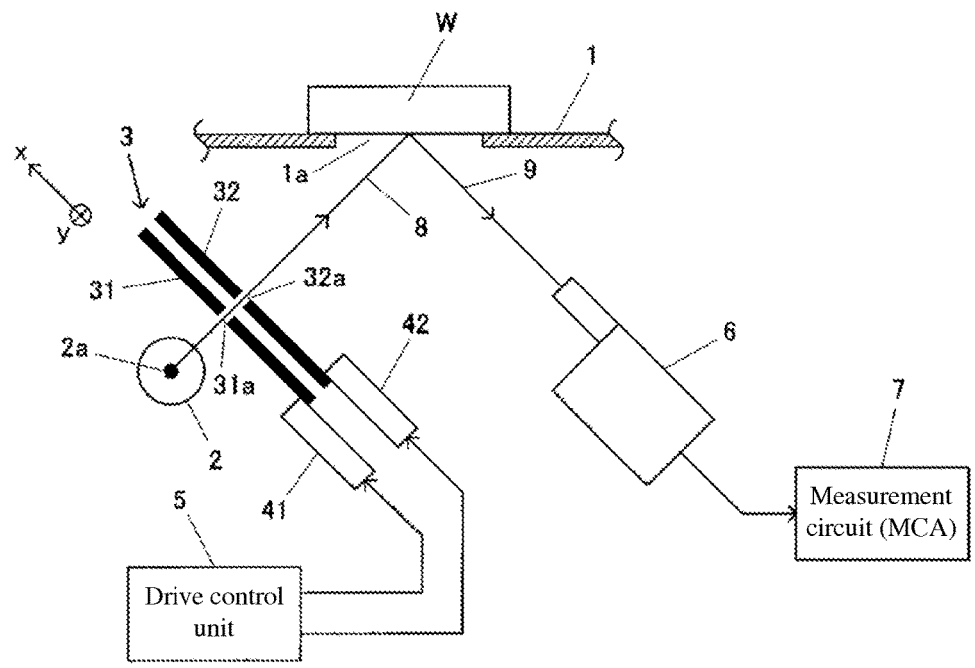

FIG. 1 is a diagram of the main parts of an embodiment of the present invention, in which a schematic representing the mechanical configuration is shown in combination with a block diagram representing the system configuration.

A sample W is supplied for analysis in a state where it has been placed on a sample tray 1. A cutout part 1a is formed in the sample tray 1, the sample W is placed onto the sample tray 1 so as to cover this cutout part 1a, and excitation X-rays 8 are irradiated toward the bottom surface of the sample W through this cutout part 1a.

The excitation X-rays 8 are X rays, wherein the X-ray from the X-ray tube 2 is made to pass through collimator unit 3 so as to narrow the X-ray irradiation area on the surface of the sample W to the required size, and to shape the X-rays into a bundle of substantially parallel rays. The fluorescent X-rays 9 emitted from the sample W due to irradiation of the sample W with these excitation X-rays 8 are detected by an X-ray detector 6, which comprises a semiconductor detector. The output of this X-ray detector 6, just as in the prior art, is acquired by a measurement circuit 7, based on a multichannel analyzer (MCA), and is sorted by wave height, after which signals of each wave height (energy) are counted and used for analysis of the elements contained in the sample W and their concentration.

The distinguishing characteristic of this embodiment consists in the configuration of the collimator unit 3, which in this example comprises two flat collimator plates 31 and 32 which are parallel to each other and in which through-holes 31a and 32a are respectively formed in the thickness direction. These collimator plates 31 and 32 are independently displaced in a plane along their respective directions of spread by means of displacement mechanisms 41 and 42 with which they are respectively provided. Namely, each displacement mechanism 41, 42 supports the corresponding collimator plate 31, 32, and is able to move it in the two orthogonal axial directions x and y in the drawing.

The displacement mechanisms 41, 42 are controlled and driven by a control signal supplied from a drive control unit 5, and cause the collimator plates 31, 32 to be displaced in interlocked fashion as indicated below.

Namely, the collimator plates 31, 32 are displaced so as to locate the through-holes 31a, 32a on a line connecting the focal point 2a of the X-ray tube 2 and an arbitrary point on the sample W. Then, by subjecting these collimator plates 31, 32 to interlocked displacement as described above, the irradiation location of excitation X-rays 8 on the sample W is successively changed and the fluorescent X-rays 9 at each irradiation location are detected by the X-ray detector 6 in order to perform mapping analysis, i.e. to determine the elements and concentration thereof present at each irradiation location.

The point to be noted in particular in the above embodiment is that the collimator unit 3 is composed of two collimator plates 31, 32 which are subjected to interlocked displacement, the collimator plates 31, 32 being displaced such that the through-holes 31a, 32a of each collimator plate 31, 32 are always located on a line connecting the X-ray focal point 2a to an arbitrary point on the sample W so as to thereby change the irradiation location of excitation X-rays 8 on the sample W, thus making it possible to suppress the shading of excitation X-rays rays 8 due to horizontal movement of the collimator unit 3. The operation thereof will be described below.

FIG. 2 is an illustration of the operation of the collimator unit 3 used in the embodiment of the present invention. In FIG. 2, for expediency of illustration, the collimator plates 31, 32 and the surface of the sample W are made parallel, but the result would be the same if they were non-parallel as in FIG. 1.

To move from the state where the line L1 connecting the X-ray focal point 1a and the point P1 on the sample W to be irradiated with excitation X-rays 8 is orthogonal to the collimator plates 31, 32, as shown in FIG. 2 (a), to point P2 as shown in FIG. 2 (b), the collimator plates 31, 32 are moved so as to locate the centers of the through-holes 31a, 32a of the collimator plates 31, 32 over the line L2 connecting point P2 and the X-ray focal point 1a. In this state, the excitation X-rays 8 are subjected to slight shading to the extent that the axis of the through-holes 31a, 32a is not exactly over line L2, so the X-ray irradiation region B on the sample W becomes slightly smaller than irradiation region A in FIG. 2 (a), but the amount of such shading is greatly reduced as compared to the case where a single collimator with a thickness equivalent to the total thickness of collimator plates 31, 32 is used.

Figure 3:
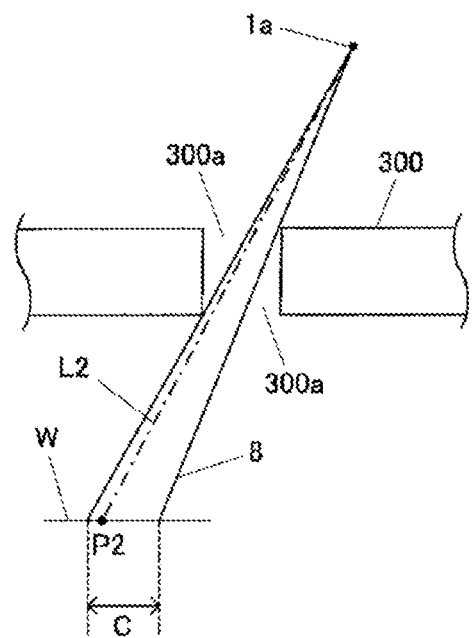

FIG. 3 is an illustration of the case where a single collimator 300 with a thickness equivalent to the total of the thicknesses of each of the collimator plates 31, 32 in FIG. 2 is used, and that collimator 300 is moved to irradiate the same point P2 on the sample W as in FIG. 2 (b) with excitation X-rays 8. The through-hole 300a of the collimator 300 in FIG. 3 is made the same size as the through-holes 31a, 32a of the collimator plates 31, 32 in FIG. 2. As is evident from this drawing, locating the center of the through-hole 300a of the collimator 300 over the line L2 connecting point P2 and X-ray focal point 1a causes the excitation X-rays 8 to be irradiated toward point P2, but here, due to the fact that through-hole 300a is tilted diagonally to line L2, a shading of the excitation X-rays 8 occurs, and the X-ray irradiation region C on the sample W becomes smaller. Comparing this irradiation region C to irradiation region B of FIG. 2 (b) in the case where the same point P2 is irradiated with excitation X-rays 8 in the embodiment of the present invention, it can be seen that irradiation region B is greater than irradiation region C. Namely, the effect of suppressing the shading of excitation X-rays 8 in the embodiment of the present invention is evident.

While in the above embodiment, an example was illustrated where two collimator plates 31, 32 were used for the collimator unit 3, an arbitrary number of collimator plates can be used.

Furthermore, in the embodiment described above, the collimator plates 31, 32 were arranged at a gap from each other, but they may also be arranged in close contact with each other.

Moreover, in the above embodiment, an example was illustrated wherein the sample W was placed on a sample tray 1 provided with a cutout part 1a, and excitation X-rays 8 were irradiated toward the bottom surface of the sample W through the cutout part 1a, but a configuration wherein the excitation X-rays are irradiated toward the top surface of the sample can of course also be used.

In addition, in the embodiment described above, an example was illustrated wherein the present invention was applied to an energy dispersive X-ray analysis device, but the present invention can of course equally be applied to a wavelength dispersive X-ray analysis device.

DESCRIPTION OF REFERENCES

1 Sample tray
1a Cutout part
2 X-ray tube
2a X-ray focal point
3 Collimator unit
31, 32 Collimator plate
31a, 32a Through-hole
41, 42 Displacement mechanism
5 Drive control unit
6 X-ray detector
7 Measurement circuit
8 Excitation X-rays
9 Fluorescent X-rays
W Sample

What is claimed:
1. An X-ray analysis device, comprising:
an X-ray tube including a collimator unit that irradiates X-rays onto a sample, said collimator unit comprises a plurality of flat collimator plates, each of said collimator plates including a through-hole formed in their thickness direction, the collimator plates are arranged parallel to each other and are configured such that each collimator plate is movable in two orthogonal directions of spread of the plates by driving of an individual displacement mechanism;

an X-ray detector that detects fluorescent X-rays generated due to such irradiation, wherein information concerning elements contained in the sample is obtained from the detection results; and a controller that drives said displacement mechanisms in interlocked fashion so as to locate the centers of the through-holes of said collimator plates on a line connecting the focal point of said X-ray tube and an arbitrary point on the sample, and so as to move the irradiation location of X-rays from said X-ray tube on the sample by moving each of said collimator plates in the two orthogonal directions such that occurrence of X-ray shadow on the sample is suppressed;

wherein the plurality of flat collimator plates are arranged between the X-ray tube and the sample.

2. The X-ray analysis device according to claim 1, wherein each of said collimator plates is moved in two orthogonal directions.

3. The X-ray analysis device according to claim 1, wherein said collimator plates comprises three or more collimator plates.

4. An X-ray analysis method, comprising:

irradiating X-rays onto a sample by an X-ray tube including a collimator unit, said collimator unit comprises a plurality of flat collimator plates, each of said collimator plates including a through-hole formed in their thickness direction, the collimator plates are arranged parallel to each other and are configured such that each collimator plate is movable in two orthogonal directions of spread of the plates by driving of an individual displacement mechanism;

detecting fluorescent X-rays generated due to such irradiation by an X-ray detector, wherein information concerning elements contained in the sample is obtained from the detection results; and driving said displacement mechanisms in interlocked fashion so as to locate the centers of the through-holes of said collimator plates on a line connecting the focal point of said X-ray tube and an arbitrary point on the sample, and so as to move the irradiation location of X-rays from said X-ray tube on the sample by moving each of said collimator plates in the two orthogonal directions such that occurrence of X-ray shadow on the sample is suppressed;

wherein the plurality of flat collimator plates are arranged between the X-ray tube and the sample.

5. The X-ray analysis method according to claim 4, wherein each of said collimator plates is moved in two orthogonal directions.

6. The X-ray analysis method according to claim 4, wherein said collimator plates comprise three or more collimator plates.

* * * * *